United States Patent [19]

Benzaria et al.

[11] Patent Number: 5,545,746
[45] Date of Patent: Aug. 13, 1996

[54] METHOD FOR RECOVERY OF ALKALI METAL OR ALKALINE-EARTH METAL TEREPHTHALATE AND OF ALKYLENE GLYCOL FROM POLYETHYLENE TEREPHTHALATES

[75] Inventors: Jacques Benzaria, Chambly; Francois Dawans, Bougival; Bruno Durif-Varambon, Vienne; Jean-Bernard Gaillard, St. Martin D'Heres, all of France

[73] Assignee: Institut Francais du Petrole, Rueil Malmaison, France

[21] Appl. No.: 367,859

[22] Filed: Jan. 3, 1995

Related U.S. Application Data

[63] Continuation-in-part of Ser. No. 149,405, Nov. 9, 1993, abandoned.

[51] Int. Cl.[6] ............................................. C07C 67/48
[52] U.S. Cl. ............................ 560/78; 562/483; 562/485; 562/487; 562/480
[58] Field of Search ............................ 562/480, 483, 562/485, 487; 560/78

[56] References Cited

U.S. PATENT DOCUMENTS 3,544,622  12/1970  England ................................. 260/515
4,890,996  1/1990  Shimizu ................................. 425/145
5,254,666  10/1993  Benzaria ............................... 528/272

FOREIGN PATENT DOCUMENTS 0037984  10/1981  European Pat. Off. .
2342152  2/1977  France .
2802125  7/1979  Germany .
1130695  3/1967  United Kingdom .

Primary Examiner—C. Warren Ivy
Assistant Examiner—Rosalynd A. Williams
Attorney, Agent, or Firm—Millen, White, Zelano, & Branigan, P.C.

[57] ABSTRACT

An improved method for recovery of alkali metal or alkaline-earth metal terephthalate and of alkylene glycol, from polyalkylene terephthalate, in particular from polyethylene terephthalate (P.E.T.), alkylene glycol, in particular ethylene glycol produced in the form of vapor during the saponification reaction, initiated by the action of intensive kneading of polyalkylene terephthalate and the alkaline reagent at a temperature of 100° to 200° C. The alkylene glycol is recovered in gaseous form by entrainment by an inert gas or by extraction under low pressure. The alkaline terephthalate or alkaline-earth terephthalate is obtained in solid or powder form; it can easily be stored, transported and redissolved, in order to be purified and possibly transformed into terephthalic acid or ester.

24 Claims, No Drawings

METHOD FOR RECOVERY OF ALKALI METAL OR ALKALINE-EARTH METAL TEREPHTHALATE AND OF ALKYLENE GLYCOL FROM POLYETHYLENE TEREPHTHALATES

This application is a continuation-in-part of U.S application Ser. No. 08/149,405, filed Nov. 9, 1993, now abandoned.

BACKGROUND OF THE INVENTION

The invention relates to an improved method for the recovery of terephthalates of alkali metals or alkaline-earth metals or of terephthalic acid and of alkylene glycol by saponification of a polyalkylene terephthalate. It relates more particularly to the continuous production of terephthalates of alkali metals or alkaline-earth metals from polyalkylene terephthalates.

It allows improved recycling of polyalkylene terephthalate waste originating, for example, from films, fibers or used bottles. The method according to the invention further allows recovery of alkylene glycol of good purity, for re-use.

Alkaline saponification of polyalkylene terephthalate in solution is described in the prior art (see, for example, U.S. Pat. No. 3,317,519 and U.S. Pat. No. 3,544,622); it is generally performed in solution diluted in water or in glycol, generally under pressure.

In patent application French Patent No. 2,672,049,the applicants have described a method for manufacturing terephthalates of alkali metals or alkaline-earth metals by heating polyalkylene terephthalate with an alkali metal hydroxide or an alkaline-earth metal hydroxide, in the absence or the presence of water.

SUMMARY OF THE INVENTION

It has now been discovered that it was possible to carry out saponification with an alkaline hydroxide or alkaline-earth hydroxide of polyalkylene terephthalate without solvent or dilutant, in a molten state, while removing the alkylene glycol formed, the alkaline terephthalate or alkaline-earth terephthalate recovered being obtained in powder form.

It was accidentally discovered that the saponification reaction between a polyalkylene terephthalate and an alkaline hydroxide or alkaline-earth hydroxide, primed by previous heating of the mixture of reagents to a temperature of 60° to 250° C. carries on by itself, without supplementary heating. The polyterephthalate continues to react until the end of the reaction, even without stirring, to form a product soluble in water without any trace at all of the original polymer.

The main advantage of the method according to the invention is that it allows continuous production of an alkaline or alkaline-earth terephthalate compound in powder from and to eliminate the stage of recovery of the alkylene glycol in purifying waters. The powdery solid obtained is easy to store, to transport and to redissolve later in an aqueous phase with a view to purification thereof, and if required, of its transformation into terephthalic acid or ester.

The removal of alkylene glycol in gaseous form odor to dissolving the metal alkali terephthalate facilitates the purification of the latter by the dissolving in particular certain colorants and soluble products in alkylene glycol.

In the prior art, the glycols produced by saponification were either extracted from the solution with the aid of a solvent, after filtration of the terephthalic acid, or by salting out by saturation of the solution by increasing the salinity of the medium, or were otherwise sent to the sewage treatment plant. These methods amounted to a supplementary operation which was costly in terms of reagents, matedal and time. The method according to the invention allows removal of the glycol formed without supplying additional reagent, either by entrainment by means of an inert gas or by low pressure extraction during the saponification reaction, which simplifies the desired outline of the production of alkali metal or alkaline-earth metal terephthalate.

With regard to the odor art, the method according to the invention allows processing of polyester waste in small, non-localized, simple industrial units and subsequent collection together of the saponification products, comprising essentially of mono and di-alkaline or alkaline-earth terephthalates coming from different sources, for processing in a single industrial installation with a view to purifying them and transforming them into reusable terephthalic acid or ester by polycondensation. Such an operation, carried out in two distinct stages, reduces investment and the costs for collection and transport of plastics waste.

The method according to the invention allows alkali metal or alkaline-earth metal terephthalates to be obtained industrially and in a more economical manner, from which terephthalic acid or ester of great purity can be made. This technique has proved particularly important for film, fibers or polyethylene terephthalate (PET) bottle recycling.

The method according to the invention principally involves carrying out saponification by an alkali metal or alkaline-earth metal hydroxide, without solvent or dilutant, in a molten state, the reaction being stimulated by continuous passage of a solid mixture or polyterephthalate and of alkali-metal or alkaline-earth metal hydroxide in a heated kneader-extruder which is specially equipped to remove vapor, and/or then being continued, outside this first kneader-extruder, in a thermally controlled vessel, stirred and kept at low pressure in order to remove the glycol formed, the glycol also being able to be entrained by a current of inert gas, but operating at a higher temperature.

In general, the method according to the invention can be defined by the fact that a) the initial compound, principally composed of polyalkylene terephthalate, is mixed with an alkali metal or alkaline-earth hydroxide which is, in practice, anhydrous, in the absence of solvent;

b) the mixture obtained is heated, said mixture being at least in part molten, in such a manner as to stimulate the saponification of polyalkylene terephthalate;

c) the alkylene glycol formed during the saponification reaction is removed; and d) the alkali metal or alkaline-earth terephthalate is recovered in the form of a powdery material.

The method according to the invention is described in more detail hereafter.

Polyalkylene terephthalate, consisting for example of film, fiber or bottle waste is previously ground or shredded and intimately mixed with fibers with an alkali metal or alkaline-earth metal hydroxide in the form of powder, granules, chips, or pellets, these reagents being metered in such a manner that the alkali-metal or alkaline-earth metal reagent is in stoichiometric proportion or slightly in excess thereof, with respect to the carboxylic groupings of the polyalkylene terephthalate. The reagents are introduced, for example by gravity, into a reactor which can be a continuously operating kneader-extruder.

In the case of a continuous kneader-extruder, introduction of reagents at the start of the kneading chamber permits advantage to be taken of the whole length of time spent in the kneader, it is also possible, without departing from the scope of the invention, to introduce all or some of the reagents later of at various places.

The introduction outputs are variable and are a function of the reaction conditions, of the size and type of kneader-extruder and of the time spent by the reagents required to stimulate saponification. In general they are in a range of between 50 and 10,000 kg/h with a kneader-extruder of 5 inches×36 inches taken as a reference.

By using the hysterisis effect, a further advantage of the method according to the invention is obtained, in that very high outputs can be achieved in a small volume kneader-extruder reactor, by stimulating saponification and by inducing the continuation of the reaction until its completion, which can then be carried out in equipment simplified by virtue of making use of the exothermic nature of the reaction.

The mixture and the homogenization of the reagents necessary to stimulate saponification is carried out at a temperature within the range of 60° and 250° C., and preferably between 100° and 200° C. and more specifically, between 120° and 160° C. in order to avoid formation of secondary degradation products.

More particularly, the reaction takes place at a satisfactory rate at around 150° C. and preferably the temperature is controlled by circulation of cooled fluid. The reactor is fed with a mixture of polyalkylene terephthalate (particularly P.E.T) and hydroxide (particularly sodium carbonate) by means of a meter.

Mixing in the kneader-extruder reactor can be undertaken by different arrangements of blades along two parallel shafts rotating in the same direction, or not, within a double-screw kneader-extruder. Generally a careful selection of the arrangement of blades comprises on the one hand, at the entrance to the kneading chamber, self-cleaning endless screws which ensure the introduction of gravity fed reagents, and on the other hand several types of mixing blades, for forward movement, for shearing and for delay in order to have optimum mixing, homogenization and kneading capability, adapted to the saponification process.

According to a preferred method for carrying out the invention, saponification is stimulated by associating heating and the hysterisis effect on the mixture of polymer and alkali metal or alkaline-earth metal hydroxide. According to the degree of hysterisis, the temperature of the mixture is increased by mechanical working which allows the energy produced by working the material to be used and time spent in the kneader-extruder reactor to be reduced.

According to a variation of the method, the alkylene glycol is continuously removed from the kneader-extruder reactor under low pressure and/or by entrainment by means of an inert gas, which can be nitrogen, then condensed by cooling.

According to another variation of the invention, at the outlet of a kneader-extruder reactor, the reaction mixture is de-gassed, the glycol being removed under low pressure and/or by entrainment by means of a stream of inert gas; the glycol vapors formed are then condensed. This second step of the method according to the invention is preferably performed while the mixture from the kneader extruder is maintained at a temperature range of between 50° and 200° during a period of time sufficient to complete the saponification, for example from 5 to 30 minutes. This stage can be carded out by passing the mixture through a single-screw reactor or on a heated conveyor or otherwise in a vessel, which allow temperature to be maintained and the glycol formed to be collected.

By way of an example, the outlet of the kneader-extruder reactor is connected to a sealed heating chamber provided with a double-screw, by means of a sealed distributor. The mixture continues to react; the glycol is extracted under low pressure and/or by entrainment. The time spent in this screw can be within the range of 10 minutes and 2 hours. Output of the finished product can be done by a sealed extractor. The terephthalate obtained can now be stored, or in the case of an alkali metal terephthalate, placed in aqueous solution for subsequent purification. According to a particular type of production according to the invention, stimulation or initiation of the saponification reaction is carded out in a kneader-extruder with double corotating screws and the reaction is completed in a powder kneader, which can be provided with a screw or "Z" arm, in a stream of inert gas for entrainment of the glycol formed which is condensed outside the reactor.

The continuous removal, preferably under low pressure, of the glycol formed during saponification constitutes a further improvement according to the invention; it allows more complete saponification to be obtained than using the operating modes of the prior art, and an increase in the reaction speed. In this way, conversion of 95% in weight or more polyterephthalate into terephthalic acid salt is obtainable.

Contrary to the methods of the prior art, which lead to dilute solutions of alkali-metal or alkaline-earth metal terephthalates being obtained, the method according to the invention allows concentrated terephthalates to be obtained, in the form of a powdery solid which is more easily stored and transported, and the alkali-metal terephthalates (for example, sodium) being directly soluble in water.

Another major advantage of the method according to the invention is that it has low sensitivity to the possible presence of other polymers, such as polyolefines or polyvinyl chloride, mixed with the polyterephthalate. Consequently the method according to the invention is particularly suitable for recycling PET waste from ground or shredded used bottles or flasks.

During saponification of polyterephthalate waste from packaging, films, fibers or bottles, various other impurities can be present, such as fillers, additives, colorants, wrappings, labels etc. The method according to the invention allows all these impurities to be separated by dissolving the saponification product in water and filtering the aqueous solution, possibly with one or more adsorbents, before acidifying the aqueous solution to precipitate the terephthalic acid.

EXAMPLES

The following examples are given by way of illustration and do not limit the present invention in any way.

EXAMPLE 1

In a 5"×36" (15KW) kneader-extruder manufactured by AOUSTIN under license from READCO, and comprising two endless screws rotating in the same direction and a temperature controlled oil circulation heating system for the body of the kneader, there is continuously added, by means of two volumetric meters, 56 kg/h of P.E.T. chips of shredded film (average particle size approximately 4×1.5 cm; apparent-density approximately 0.10) and 28 kg/h of technical quality caustic soda pellets, these outputs allowing constant maintenance of a ratio by weight of PET/NaOH of approximately 2. The temperature of the oil circulating in the double envelope of the kneader is in the range of between 150° and 160° C. at the beginning and is lowered to 120°–130° C. once the state of equilibrium is reached. The rotation speed of the double screw is 70 r.p.m. Under these conditions the average time spent by the material in the body of the kneader is estimated to be 6 minutes. A sample of the material taken from the product from the kneader-extruder indicated a saponification rate of above 60%.

This product is then de-gassed under low pressure (10 mmHg) to remove the ethylene glycol formed and it is kept at a temperature within the range of between 80° and 130° for 30 minutes by passing it over a conveyor in a heating tunnel.

In this way a powdery solid is obtained, essentially composed of mono and disodium terephthalate.

The final saponification rate is above 97%, and all of the PET used is transformed.

EXAMPLE 2

In the same apparatus used in Example 1, and according to a similar method, 235 kg/h of chipped PET waste in the form of fine grains (several mm) of apparent density of approximately 0.6, and 110 kg/h of pelleted caustic soda is processed. Under these conditions, all things being equal in other respects to Example 1, the time spent by the metal in the body of the kneader is less than 2 minutes. The rate of saponification obtained under these conditions is approximately 40%.

The product exiting the kneader-extruder with double corotating screws is subsequently introduced into a single-screw kneader which is 4.5 meters in length, kept at a temperature of approximately 150° C. and swept by a stream of nitrogen for entrainment of the ethylene glycol vapors formed which are then condensed and recovered.

The powdery solid produced is tipped into an excess of water to obtain an aqueous solution diluted (for example 140 g/l) by sodium terephthalates. This solution is passed into a column containing active carbon; it is then acidified with sulphuric acid to obtain a pH of approximately 2.5 to 3. The terephthalic acid which precipitates is filtered and washed in water, then dried.

The conversion of PET into terephthalic acid is above 97% and the purity of the acid obtained is above 99.5%, this acid being in any case usable as an acid of polymer quality.

EXAMPLE 3

As in Examples 1 and 2, 38.6 kg/h of caustic potash and 54 kg/h of PET pellets from shredded used bottles and containing in the order of 10% by weight of polyethylene and polyvinyl chloride is processed. The speed of rotation of the screw is 200 rpm. The rate of saponification obtained under these conditions, all things being equal in other respects, and calculated with respect to the weight of PET used, is above 50% at the outlet of the double-screw kneader-extruder and above 95% after processing according to the same operating mode as in Example 2.

EXAMPLE 4

2,000 of chipped PET polyester from films are cold mixed in a band mixer with 926 kg of sodium carbonate at a minimum of 98%, that is to say approximately 10% above the stoichiometric quantity.

The mixture of reagents is fed by means of a meter into a double-screw kneader-extruder preheated to 150° C., the outlet of which is connected by means of a rotary obturator to a double Archimedes screw in a dosed thermally controlled tank, in which the product stays for ½ an hour—the whole being evacuated—and the tank outlet is via a sealed obturator so that the vacuum inside the tank is maintained.

The meter for the initial mixture is staded; as soon as the kneader-extruder reaches the temperature of 150° C. the reaction takes place and the oil circulation is controlled in such a way that the temperature does not exceed 150° C. As soon as the endless screw is fed, a vacuum in the order of 20 mm Hg is applied. The glycol distills and the sodium terephthalate transforms into a very fluid, non-adhesive powder which is free of glycol. This glycol is recovered by condensation and is of sufficient purity for use in refrigeration fluids.

Yields observed with respect to the PEET contained in the initial product:

| Extract of sodium terephthalate | 2150 kg (Yield 98%) |
|---|---|
| Ethylene glycol | 601 kg (Yield 93%) |

We claim:

1. A method for recovering alkali metal or alkaline-earth metal terephthalate from an initial composition comprising a polyalkylene terephthalate, said method comprising:
    a) mixing the initial composition with an anhydrous alkali metal or alkaline-earth metal hydroxide in the absence of a solvent to form a mixture;
    b) heating the resultant mixture, said mixture being at least in part in a molten state, to a temperature effective to initiate saponification of the polyalkylene terephthalate and to sustain the reaction to completion without further heating;
    c) removing in gaseous form the resultant alkylene glycol formed during the saponification reaction and;
    d) recovering the resultant alkali-metal or alkaline-earth metal terephthalate from the saponification reaction in the form of a powdery product.

2. A method according to claim 1, wherein all of the operations are carded out non-continuously or continuously.

3. A method according to claim 1, the saponification reaction is initiated in a reactor using the effect of hysterisis and the subsequent increase in the temperature of the mixture.

4. A method according to claim 3, wherein the initial mixture is passed into a kneader-extruder reactor where the initial mixture is subjected to a transfer of thermal energy by the effect of hysterisis, whereby the saponification reaction is initiated.

5. A method according to claim 4, wherein the saponification reaction is initiated by a process comprising introducing a solid mixture of polyalkylene terephthalate and alkali metal or alkaline earth metal hydroxide into a kneader-extruder reactor with or without double corotating screws.

6. A method according to claim 5, wherein the initial mixture is continuously fed into a kneader-extruder reactor with double corotating screws with an arrangement of blades for entry, mixing, moving forward, shearing and delay, allowing homogenization and heating of the reaction mixture sufficient to bring about the saponification process.

7. A method according to claim 1, wherein the initiation temperature for the saponification reaction is in the range of 60° to 250°.

8. A method according to claim 1 wherein the alkylene glycol formed during the saponification reaction is continuously removed.

9. A method according to claim 1 wherein the alkylene glycol formed is removed by entrainment or by removal under low pressure.

10. A method according to claim 1 wherein the alkylene glycol formed is removed at least in part in the kneader-extruder reactor.

11. A method according to claim 1, wherein the polyalkylene terephthalate is a polyethylene terephthalate (PET), and the alkylene glycol is ethylene glycol.

12. A method according to claim 1 wherein the initial polyalkylene terephthalate is comprised of packaging, film, fiber or bottle waste.

13. A method for recovering terephthalic acid, comprising:
   a) mixing polyalkylene terephthalate with an anhydrous alkali metal or alkaline-earth metal hydroxide in the absence of a solvent to form a mixture;
   b) heating the resultant mixture, said mixture being at least in part in a molten state, to a temperature effective to initiate saponification of the polyalkylene terephthalate and to sustain the reaction to completion without further heating;
   c) removing in gaseous form the resultant alkylene glycol formed during the saponification reaction;
   d) recovering the resultant alkali-metal or alkaline-earth metal terephthalate from the saponification reaction in the form of a powdery product, and;
   e) producing terephthalic acid by dissolving the alkali metal or alkaline earth metal terephthalate in water and acidifying.

14. A process for the production of alkali metal or alkaline-earth metal terephthalate comprising heating an at least partly molten mixture of anhydrous alkali metal or alkaline-earth metal hydroxide and polyalkylene terephthalate in the absence of a solvent to a temperature effective to initiate saponification and maintain the reaction to completion without further heating.

15. A process according to claim 14, further comprising removing resultant alkylene glycol in gaseous form.

16. A method according to claim 4, wherein the saponification reaction thus initiated is continued within said kneader extruder reactor.

17. A method according claim 4, wherein the saponification reaction thus initiated is continued outside said kneader extruder reactor.

18. A method according claim 17, wherein the reaction is continued in a sealed heating chamber.

19. A method according to claim 17, wherein the reaction is continued in a powder kneader.

20. A method according to claim 4, wherein the reactor contains a kneading chamber having a first end and a second end, and the polyalkylene terephthalate and the hydroxide are introduced at the first end.

21. A method according to claim 4, wherein the reactor contains a kneading chamber having a first end and a second end, and the polyalkylene terephthalate and the hydroxide are introduced after the first end.

22. A method according to claim 1, wherein the initiation temperature for the saponification reaction is in the range of 100° to 200°.

23. A process for the production of alkali metal or alkaline-earth metal terephthalate, comprising determining a temperature effective to initiate saponification and maintain to completion a saponification reaction between an at least partly molten mixture of anhydrous alkali metal or alkaline earth metal hydroxide and polyalkylene terephthalate in the absence of a solvent, and heating such a mixture to said temperature.

24. A method according to claim 1, wherein all of the operations are carried out continuously.

* * * * *